(12) United States Patent
Simonette

(10) Patent No.: US 7,494,548 B2
(45) Date of Patent: Feb. 24, 2009

(54) METHOD OF CLEANING CONTACT LENSES VIA SONICATION

(76) Inventor: Rebecca Ann Simonette, 4615 N. Braeswood Blvd., #307, Houston, TX (US) 77096

( * ) Notice: Subject to any disclaimer, the term of this patent is extended or adjusted under 35 U.S.C. 154(b) by 0 days.

(21) Appl. No.: 11/704,120

(22) Filed: Feb. 8, 2007

(65) Prior Publication Data
US 2008/0190447 A1 Aug. 14, 2008

(51) Int. Cl.
B08B 3/12 (2006.01)

(52) U.S. Cl. .......................... 134/1; 134/901

(58) Field of Classification Search ............ 134/1, 134/18, 32, 34, 42, 901
See application file for complete search history.

(56) References Cited

U.S. PATENT DOCUMENTS

| | | | |
|---|---|---|---|
| 3,720,402 A | * | 3/1973 | Cummins et al. ............ 366/114 |
| 3,851,861 A | | 12/1974 | Cummins et al. |
| 3,973,760 A | * | 8/1976 | Browning et al. ............ 366/111 |
| 4,382,824 A | | 5/1983 | Halleck |
| 4,607,652 A | | 8/1986 | Yung |
| 4,697,605 A | | 10/1987 | Yung |
| 4,991,609 A | | 2/1991 | Browning |
| 5,129,410 A | | 7/1992 | Ifejika |
| 5,178,173 A | * | 1/1993 | Erickson et al. ............. 134/184 |
| 6,183,705 B1 | | 2/2001 | Chang |
| 6,193,806 B1 | | 2/2001 | Reed |

FOREIGN PATENT DOCUMENTS

| JP | 63-33726 | * | 2/1988 |
|---|---|---|---|
| JP | 09-225010 | * | 9/1997 |

* cited by examiner

*Primary Examiner*—Michael Kornakov
*Assistant Examiner*—Stephen Ko

(57) ABSTRACT

A process for cleaning all types of contact lenses by placing each contact lens in individual compartments of a liquid impermeable lens storage container filled with an aqueous medium such as sterile saline or sterile lens cleaning solution, floating the liquid impermeable storage container in an ultrasonic device operating at a frequency of 50-60 Hz and a wattage of 20-117 watts.

6 Claims, 1 Drawing Sheet

METHOD OF CLEANING CONTACT LENSES VIA SONICATION

BACKGROUND

There are many techniques for cleaning and sterilizing contact lenses. Contact lenses continue to be fragile and collect surface contaminants that diminish the visual capacity and useful nature of the contact lenses. Statistics show that the majority of contact lens wearers do not comply with proper cleaning and handling of contact lenses. This new method of cleaning facilitates the cleaning and disinfecting process and improves the visual clarity of the lenses for the wearer, for the recommended life of the contact lenses, in a manner that is simple, economical and quick.

Some wearers of contact lenses bypass the various cleaning processes by purchasing new lenses that are worn a few days and then disposed. This system is good for contact lens manufacturers but wasteful and expensive for the wearer.

Other wearers scrub their lenses with their fingers or use non-scrub cleaners and enzymatic drops or enzymatic soaking tablets to try to clean their contact lenses. These chemicals are costly, can be difficult to remove from the surface of the lenses and irritating to the eyes of the wearer. They can contribute to allergic reactions and eye infections. Some of the enzymatic cleaners are made from porcine pancreatic enzymes, which are against dietary laws for some wearers. Often during the cleaning process, the wearers can have the misfortune of tearing their lenses because of excess handling. Dissatisfaction with these processes of cleaning contact lenses has helped to fuel the disposable line of lenses. Surface contaminants on contact lenses can be from external sources like dirty fingers, air borne particles or from eye discharge that can consist of protein deposits or lipid and mucoid products produced by tears. Bacteria and fungal deposits have been found on contact lenses. In the lab, scientists have been unable to reproduce fungal growth on contact lenses. In April of 2006, there was a fungal outbreak among contact lens wearers, and in November 2006, there was a bacterial outbreak in some lens cleaners that had to be recalled. This method of cleaning, because of its simplicity and effectiveness can help contact lens wearers remove unhealthy contaminants on the surface of the contact lenses. This consequently, improves the clarity of the contact lenses for the recommended life of the particular type of contact lenses, and also protects the vision of the wearers.

The use of ultrasonic waves and other cleaning techniques for contact lenses has been described in the following relevant patents.

U.S. Pat. No. 3,720,402 Cummins, describes cleaning contact lenses in a "foraminous" container within a beaker filled with saline that heats and uses ultrasonic and timing means. The process of cleaning in this manner takes two hours.

U.S. Pat. No. 3,851,861 Cummins, describes an ultrasonic cleaning device that switches off above 75 degrees centigrade, to prevent damage to the lens and the heat shortens the cleaning cycle to 15-30 minutes.

U.S. Pat. No. 3,973,3760 Browning et al, uses a membranous contact lens capsule mounting to a receptacle in contact with a tuner or to a transducer element with ultrasonic means and has a 2-minute ultrasonic cycle followed with a 20-minute disinfecting cycle.

U.S. Pat. No. 4,382,824 Halleck cleans using a combination of ultrasonic waves with a heated bath.

U.S. Pat. No. 4,607,652 Yung, describes a small battery powered ultrasonic device portable and with a removable contact lens case that fits into a cavity contained within the device that operates at a frequency of 20-40 kHz. According to the inventor, the resonance of the ultrasonic apparatus helps to sterilize the contact lenses.

U.S. Pat. No. 4,697,605 Yung uses the waste heat generated by the device described in the previous patent to heat the cleaning liquid in the cavity of the device.

U.S. Pat. No. 4,991,609 Browning, uses an ultrasonic and heating method for cleaning toothbrushes with filter means to allow separation of particulate matter followed by a 30-minute heat cycle at 65 degrees centigrade.

U.S. Pat. No. 5,129,410 Ifejika describes a rotating agitating device operating at a frequency of 10-100 Hz using electromagnetic reciprocating means to produce high energy vibrations to shake lenses clean in a rotational or linear method.

U.S. Pat. No. 6,183,705 Ching-Tsiai Chang, describes suspending contact lenses in a cleaning cup that fits into a chamber that provides ultrasonic and heating means and has a 20-30 minute cleaning cycle. The contact lenses are covered with a grille that allows the substance adhering to the lenses to be removed and to settle to the bottom of the cleaning medium. The heating means follow the ultrasonic cleaning means.

U.S. Pat. No. 6,193,806 Reed, uses a torsion spring that causes high amplitude vibrations to dislodge contaminants of the surface of the lenses.

There are several patents in the prior art that describe the use of ultrasonics as a cleaning method for metals and other hard surface materials. Ultrasonics has also been described in the literature as a method of cleaning hard plastics. It has been described as effective for metals, glass, ceramic and dense plastics and ineffective for soft materials like rubber, Styrofoam, and soft stones like pearls and opals. In directions for operating jewelry sonicators, consumers are specifically advised not to put soft stones like pearls in the cleaners that operate at 20 watts or higher power because of cracking and discoloration that can happen.

This method of cleaning contact lenses using ultrasonic waves, is distinguished from prior art because it is simple, works well with water and only requires a small amount of sterile saline or a small amount of contact lens solution. This method takes only a few minutes of time and is economical after the initial purchase of the ultrasonic device. This method can accommodate all varieties of store bought standard non-porous contact lens containers. When the Bradford protein analysis, a dye technique to determine protein deposits, is tested with this method, the contact lenses remain protein free. Additionally, this method helps to keep the contact lens storage container clean. This method is suited for people who develop allergic reactions to chemicals found in over the counter contact lens cleaning and disinfecting solutions and wetting drops. This method is successful without relying on a subsequent heating cycle. This method is successful with 'soft' lenses because the lenses are protected during the ultrasonic process, by floating in a cushion of liquid within their liquid impermeable lens container.

SUMMARY OF THE INVENTION

The present invention relates to a method for the ultrasonic cleaning of contact lenses. An ultrasonic cleaning device with a housing for an aqueous liquid is filled with a suitable aqueous medium such as water to a fill level that allows for free movement of a standard two chambered liquid impermeable contact lens case. With the elimination of the need to have the contact lens container conform to a fitted compartment within the ultrasonic unit, the design of the ultrasonic unit is simplified, various ultrasonic units readily available can be utilized and accommodation of all sizes and shapes of contact lens cases is allowed. For this method, the contact lenses are removed from the wearers eyes and placed in the respective left and right chambers of the standard lens case, then an aqueous medium such as sterile saline or contact lens solution is added to cover the contact lenses. The covers of the standard lens chambers are tightened over each chamber so the contact lenses are secured within the contact lens case. The contact lens case is now liquid impermeable and buoyant. The contact lens case is suspended in a free-floating manner in the aqueous housing of the ultrasonic device. The ultrasonic device operates at a frequency of 60 hz and produces at least 20 watts for a six-minute time span. Units operating at lower frequencies and producing less wattage do not clean contact lenses effectively. The ultrasonic device may operate at a higher frequency with success. At a maximum frequency of 50-60 hz and 117 watts, the contact lenses can be cleaned with a shortened time span of one minute. The ultrasonic device can be compact in nature, as long as free movement of the floating contact lens storage container is permitted. This cleaning method has been determined by experimenting with several different types of jewelry ultrasonic cleaners for home use and with ultrasonic cleaners manufactured for industry use. It has been determined that the store bought jewelry cleaning unit model SI414 designed by SHARPER IMAGE stores, which operates at 60 Hz and 20 watts can clean contact lenses in a 5-6 minute cycle. It has also been determined that other home jewelry cleaners like the PREMIER Princess Electro-Sonic Jewelry cleaner which operates at 8 watts are ineffective at cleaning contact lenses with this method. The company BRANSONIC makes several models of ultrasonic cleaners of varying shapes and sizes for industry use. Model B220 operates at 50-60 Hz and 117 watts and cleans effectively in a 1-minute cycle. There are several ultrasonic units readily available for purchase that allow for rapid cleaning of contact lenses that are manufactured by various companies. The ultrasonic device for this method of use has a switch that turns on the ultrasonic device with timing means so that the ultrasonic vibrations turn off when the timing means reach zero. This is a standard feature of most ultrasonic devices. When ultrasonic vibrations are completed, the wearer can put fresh sterile saline or fresh cleaning solution in the contact lens container or leave the lenses as they are and wear them at a later time. This simple method cleans contact lenses in an efficient, economical manner, prolonging the life of the contact lenses and the comfort of the wearer. This method also helps to keep the contact lens storage case clean. This method when used with sterile saline only, without chemicals, is hypoallergenic and suited for people who develop allergies to the various over the counter contact lens chemical storage solutions and cleaning liquids.

DETAILED DESCRIPTION OF THE INVENTION

Figure 1:
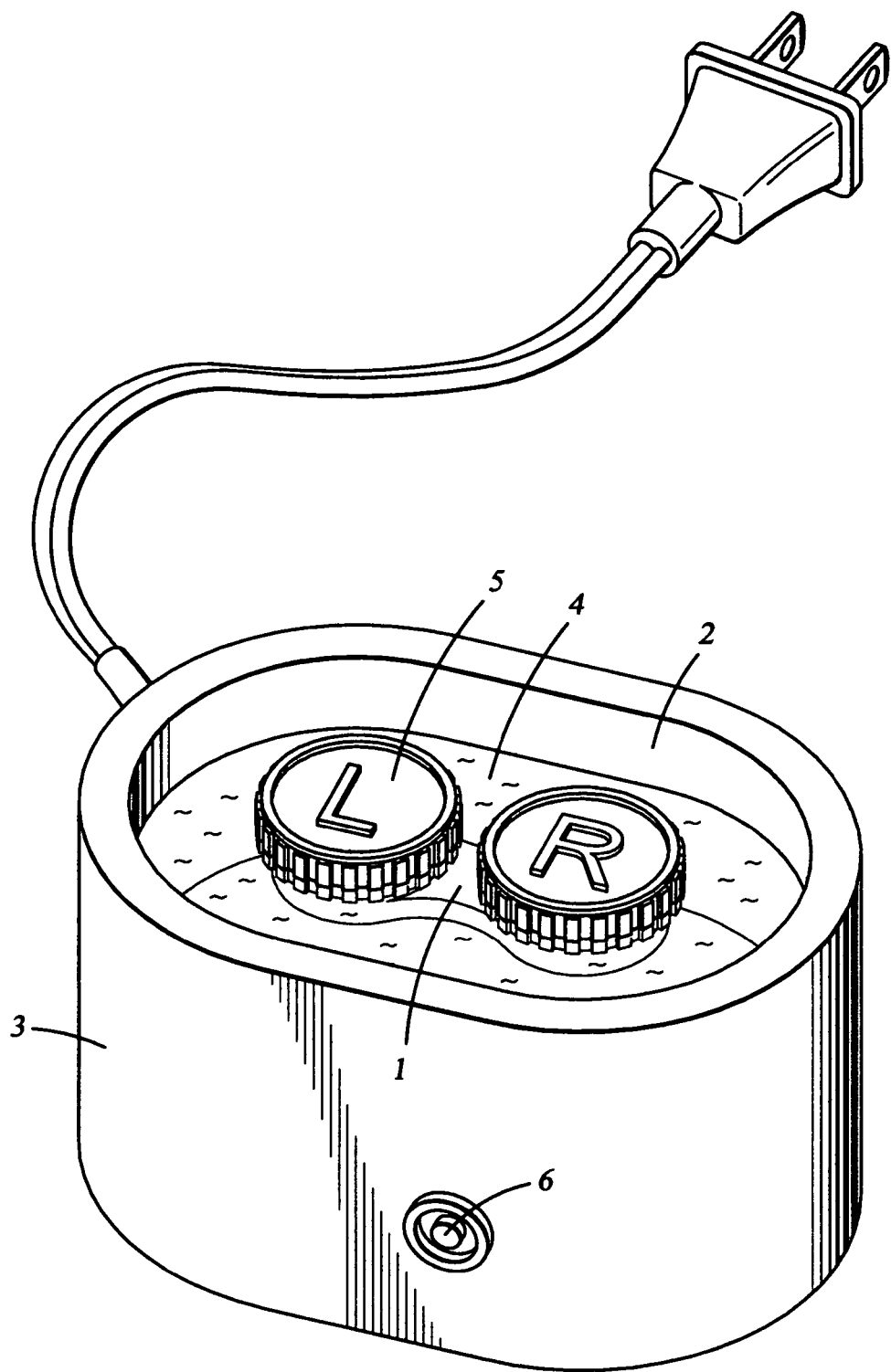
FIG. 1 shows a top view of the invention with contact lens case suspended in an aqueous medium within the housing of an ultrasonic device.

The present invention is a process for cleaning contact lenses. The contact lenses are placed within their respective lens chambers 5 in a standard liquid impermeable contact lens storage case 1, The contact lenses are then covered with an aqueous medium such as sterile saline or contact lens cleaning and disinfecting solution. The right and left corresponding liquid impermeable covers of the filled contact lens chambers 5 are placed over their respective chambers 5 and securely fastened so the lenses are housed in a buoyant liquid impermeable manner. The contact lens case 1, is then placed in the housing 2 of ultrasonic device 3, said housing being filled with an aqueous medium 4, preferably water, so said aqueous medium 4 completely surrounds and suspends said contact lens case 1. Said ultrasonic device 3 having timing means 6, which activate ultrasonic waves that vary in strength depending on the power of said ultrasonic device 3, with the minimal frequency and power of 50-60 Hz and 20 watts, cleaning in a six minute cycle and the maximum frequency of 60 Hz and 117 watts cleaning in a one minute cycle. Said timing means 6, functioning by both turning on said ultrasonic device 3 and automatically turning off said ultrasonic device 3 after set time has expired. Said contact lens case 1 is removed from aqueous medium 4 and can be left undisturbed until ready to wear, or the right and left corresponding nonporous covers of the filled contact lens chambers 5, can be removed and the chambers 5 can be refilled with new sterile saline or contact lens cleaning and disinfecting solution, and then recovered until ready to use.

What is claimed is:

1. A method of cleaning contact lenses using a container with ultrasonic means, housing means and timing means, said container having an aqueous medium in said housing means for suspending a liquid impermeable contact lens storage case, said contact lens storage case housing at least one contact lens suspended in an aqueous medium within said contact lens storage case, said timing means regulating said ultrasonic means, cleaning said contact lens within said contact lens storage case by ultrasonic vibration wherein said aqueous medium surrounding said contact lens within said impermeable contact lens storage case is contact lens solution, saline, cleaner or contact lens cleaning and disinfecting solution and said container houses said aqueous medium in said housing means that is water; and wherein said impermeable contact lens storage case is suspended in a free-floating manner in the water within said container.

2. The method of cleaning in claim 1 where said ultrasonic vibration cleans said contact lens case.

3. The method of cleaning in claim 1 where said container has ultrasonic means of at least 50 Hz and 20 watts.

4. A method of cleaning a contact lens comprising:
   a) placing a contact lens in a contact lens storage case with contact solution;
   b) sealing the contact lens storage case with the contact lens therein;
   c) placing the contact lens case in a sonicator with water wherein the lens case is suspended in a free-floating manner in the water
   d) sonicating the water, contact lens case, contact solution, and contact lens; and
   e) removing said contact lens case from the sonicator;
   wherein said contact lens case is a liquid impermeable contact lens storage case and said sonicator operates at least 50 Hz and 20 watts.

5. The method of claim 4, wherein said contact solution is saline solution.

6. The method of claim 4, wherein said contact solution is cleaning and disinfecting solution.

* * * * *